(12) United States Patent
Srikanth et al.

(10) Patent No.: US 7,790,829 B2
(45) Date of Patent: *Sep. 7, 2010

(54) CURABLE AND CURED SILICONE RUBBER COMPOSITIONS AND METHODS THEREFOR

(75) Inventors: Abirami Srikanth, Karnataka (IN); Vikram Kumar, Bangalore (IN); Helmut Steinberger, Leverkusen (DE); Umapathy Senthilkumar, Bangalore (IN)

(73) Assignee: Momentive Performance Materials Inc., Albany, NY (US)

( * ) Notice: Subject to any disclaimer, the term of this patent is extended or adjusted under 35 U.S.C. 154(b) by 590 days.

This patent is subject to a terminal disclaimer.

(21) Appl. No.: 11/827,974

(22) Filed: Jul. 13, 2007

(65) Prior Publication Data

US 2009/0018261 A1  Jan. 15, 2009

(51) Int. Cl.
*C08G 77/20* (2006.01)
(52) U.S. Cl. .......................... 528/32; 528/39
(58) Field of Classification Search ............ 528/32, 528/39
See application file for complete search history.

(56) References Cited

U.S. PATENT DOCUMENTS

| | | | |
|---|---|---|---|
| 4,418,165 A | 11/1983 | Polmanteer et al. | |
| 5,869,549 A | 2/1999 | Christ et al. | |
| 6,521,290 B1 * | 2/2003 | Kudo et al. | 427/214 |
| 6,610,108 B2 | 8/2003 | Perry et al. | |

FOREIGN PATENT DOCUMENTS

| | | |
|---|---|---|
| EP | 1 236 773 A | 9/2002 |
| WO | WO 2005/095503 A | 10/2005 |

OTHER PUBLICATIONS

J.K. Floess, et al., "The use of vinyl functional aerogels for reinforcement of silicone rubbers," *Journal of Non-Crystalline Solids*, vol. 285:1-3; Jun. 2001; pp. 101-108.
Gu et al.. "Preparation of High Strength and Optically Transparent Silicone Rubber" (1998) *Eur. Polym. J.* 34:11 p. 1727-1733.
Polmanteer et al., "Novel Wet-Process Silica Prepared From Alkyl Sillicates. (1985) Part III: Use in Silocone Elastomers for Optical Applications", *Dow Corning Corp*. p. 965-972, Rubber Chem. & Tech. 58 (1985)965-972.
Kwan et al., "Synthesis and Use of Colloidal Silica For Reinforcement in Silicone Elastomers", *Dow Corning Corp*. p. 630-644, Rubber Chem. & Tech. 74 (2001)630-644.

* cited by examiner

*Primary Examiner*—Kuo-Liang Peng
(74) *Attorney, Agent, or Firm*—Dominick G. Vicari

(57) ABSTRACT

A method for producing a functionalized silica, compositions and methods for forming curable silicone rubber compositions by using the functionalized silica are also disclosed. Compositions and methods for forming cured silicone resin compositions and products having high transparency, high tensile strength, desirable percent elongation, or a combination of the foregoing properties are also disclosed.

34 Claims, No Drawings

CURABLE AND CURED SILICONE RUBBER COMPOSITIONS AND METHODS THEREFOR

FIELD OF THE INVENTION

The invention relates generally to methods for producing functionalized silica, curable silicone rubber compositions, and cured silicone rubber compositions. Further, the invention relates to curable silicone rubber compositions and cured silicone rubber compositions made from these methods. Furthermore, the invention relates to articles made using the cured silicone rubber compositions.

BACKGROUND OF THE INVENTION

Silicone rubber is a synthetic polyorganosiloxane elastomer made from a cross-linked silicone polymer that is generally reinforced with silica, such as fumed silica. Polydimethylsiloxane (abbreviated as PDMS) is a widely used silicone polymer for such purposes. Silicone rubbers are widely used in various demanding applications, such as those requiring high and low temperature stability, a wide range of hardness, chemical resistance, weatherability, electrical properties, compression set resistance, and the like. They are usually prepared by curing suitable curable silicone rubbers. Most of the currently known cured silicone rubber compositions have a low transparency to light, example, less than about 88 percent transparency, when measured on a 2.3 millimeters thick plaque using ASTM D1003 test method. Cured silicone rubbers having a high transparency to light, example, greater than 90 percent with a 2.3 millimeters thick plaque are known, however, the cured sheets made from these materials have inferior mechanical strength, i.e., less than about 4.5 megapascals, as measured using ASTM D612 test method. Some attempts have been made to increase transparency by using silicone rubbers comprising diphenylsiloxane repeat units and matching the refractive index with that of the silica filler. However, the methods are not desirable from a cost and environmental perspective, partly because the preparation of the diphenyl monomer, such as for example, octaphenylcyclotetrasiloxane has environmental issues, due in part to the possibility of generation of polychlorinated biphenyls. Irrespective of the nature of the silicone rubbers, curable silicone compositions used for preparing the cured silicone rubber compositions have high shear viscosities of greater than about 1500 pascal-second (when measured at 10 radians per second in accordance with ASTM D440 test method), which makes them difficult to be pumped, which is a disadvantage, especially from the perspective of a commercial scale process.

Therefore, there is a continuing need for methods for producing easy-to-use curable silicone rubber compositions that have a low shear viscosity, example, less than about 1500 pascal-second, when measured as described above. Further, there is a need for producing cured silicone rubber compositions and finished parts from such curable compositions, wherein the cured compositions have a high transparency of greater than about 90 percent light transmittance, an elongation of at least about 200 percent, and a tensile strength of greater than 4.5 megapascals.

BRIEF SUMMARY OF THE INVENTION

In one aspect, a method for preparing a functionalized silica is disclosed. The method comprises: mixing an aqueous alcoholic solution and a catalyst with a first portion of a first organosilicon functionalizing agent to form a first reaction mixture; reacting the first reaction mixture with a tetraalkoxysilane at a controlled rate to form a second reaction mixture comprising a sol gel silica; and further reacting the second reaction mixture with a mixture of a second portion of the first organosilicon functionalizing agent and a second organosilicon functionalizing agent to functionalize the sol gel silica to form the functionalized silica.

In another aspect, a method for forming a curable silicone rubber composition is disclosed. The method comprises: forming a functionalized silica; adding a solvent to the functionalized silica to form a suspension comprising the functionalized silica; and compounding and devolatilizing the suspension with a silicone polymer to form the curable silicone rubber composition. The functionalized silica is prepared by a method comprising: mixing an aqueous alcoholic solution and a catalyst with a first portion of a first organosilicon functionalizing agent to form a first reaction mixture; reacting the first reaction mixture with a tetraalkoxysilane at a controlled rate to form a second reaction mixture comprising a sol gel silica; and further reacting the second reaction mixture with a mixture of a second portion of the first organosilicon functionalizing agent and a second organosilicon functionalizing agent to functionalize the sol gel silica to form the functionalized silica.

In yet another aspect, a method for forming a cured silicone rubber composition is disclosed. The method comprises: forming a functionalized silica; adding a solvent to form a suspension comprising the functionalized silica; compounding and devolatilizing the suspension with a liquid silicone polymer to form a curable silicone rubber composition; and further compounding and devolatilizing the curable silicone rubber composition to form the cured silicone rubber composition. The functionalized silica is prepared by a method comprising: mixing an aqueous alcoholic solution and a catalyst with a first portion of a first organosilicon functionalizing agent to form a first reaction mixture; reacting the first reaction mixture with a tetraalkoxysilane at a controlled rate to form a second reaction mixture comprising a sol gel silica; and further reacting the second reaction mixture with a mixture of a second portion of the first organosilicon functionalizing agent and a second organosilicon functionalizing agent to functionalize the sol gel silica to form the functionalized silica.

In other aspects, a curable silicone rubber composition and a cured silicone rubber composition prepared in accordance with the methods disclosed hereinabove are also disclosed.

DETAILED DESCRIPTION OF THE INVENTION

The previously described embodiments are useful for producing curable silicone rubber compositions, which be further cured to produce articles having a high transparency of greater than 90 percent in an embodiment, a high tensile strength of greater than 5 megapascals in another embodiment, an elongation of at least 200 percent in still another embodiment, or a combination of two or more of the foregoing properties. The present disclosure may be understood more readily by reference to the following detailed description and the examples included therein. In the following specification and the claims which follow, reference will be made to a number of terms which are defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

The terms "radical" and "group", as applied to the terms "alkyl", "cycloalkyl", "aryl", "alkoxy", "aryloxy", and "cycloalkoxy" are used interchangeably through this disclosure.

As defined herein, the term "alkyl", as applied to the first and the second organosilicon functionalizing agents, refers to an array of carbon atoms that is not cyclic and is attached to the silicon atom via an $sp^3$ carbon atom. The array of carbon atoms may further comprise any combination of $sp^3$, $sp^2$, or sp hybridized carbon atoms. The array of carbon atoms may further comprise one or more heteroatoms, such as oxygen, nitrogen, and sulfur. Further, the array of carbon atoms can be monovalent, divalent, or trivalent. Examples of alkyl groups include methyl, ethyl, n-propyl, isopropyl, n-butyl, tert-butyl, isooctyl, benzyl, cyclohexylmethyl, phenethyl, alpha,alpha-dimethylbenzyl, and the like.

As defined herein, the term "aryl", as applied to the first and the second organosilicon functionalizing agents, refers to a cyclic array of $sp^2$ hybridized carbon atoms and conjugated carbon-carbon double bonds, and is attached to the silicon atom via an $sp^2$ hybridized carbon atom. The aromatic group or radical can have from one to the maximum permissible number of substituents. The aromatic radical or group can further comprise heteroatoms, such as sulfur, oxygen, and nitrogen. Examples of aryl groups include phenyl, substituted phenyl, tolyl, substituted tolyl, xylyl, mesityl, chlorophenyl, naphthyl, furyl, furylmethyl, thienyl, pyrrolyl, and the like.

As defined herein, the term "cycloalkyl", as applied to the first and the second organosilicon functionalizing agents, refers to a cyclic array of carbon atoms, and is attached to the silicon atom via an $sp^3$ hybridized carbon atom that forms part of the cyclic array of carbon atoms. The cyclic array of carbon atoms may further comprise one or more heteroatoms, such as oxygen, sulfur, and nitrogen. Further, the cyclic array of carbon atoms can be substituted with one to the maximum permissible number of substituents. Examples of cycloalkyl groups include cyclohexyl, methylcyclohexyl, trimethylcyclohexyl, phenylcyclohexyl, tetrahydropyranyl, 4-thiacyclohexyl, cyclooctyl, and the like.

As defined herein, the term "alkenyl group", as applied to the organosilicon functionalizing agents, refers to a group comprising an olefinic functional group. The alkenyl group can be such that one of the olefinic carbons is attached to the silicon atom. Some examples of this type of alkenyl groups include vinyl or ethenyl, 1-propenyl, 1-butenyl, 1-pentenyl, styrenyl, and the like. The alkenyl group can also be such that the silicon atom is attached to an $sp^3$ hybridized carbon atom with the olefinic functional group located elsewhere on the alkenyl group. Some examples of this type of alkenyl groups include 2-propen-1-yl, 3-buten-1-yl, 4-buten-1-yl, 5-hexen-1-yl, and the like. Further, each type of alkenyl group can further comprise heteroatoms, such as oxygen, nitrogen, and sulfur.

Other than in the working examples or where otherwise indicated, all numbers expressing amounts of materials, reaction conditions, time durations, quantified properties of materials, and so forth, stated in the specification and claims are to be understood as being modified in all instances by the term "about."

It will also be understood that any numerical range recited herein is intended to include all sub-ranges within that range and any combination of the various endpoints of such ranges or subranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The functionalized silica is prepared by a procedure as follows. An aqueous alcoholic solution, a catalyst, and a first portion of a first organosilicon functionalizing agent are mixed together to form a first reaction mixture. Alcohols that can be used to prepare the aqueous alcoholic solution include water-miscible alcohols, such as methanol, ethanol, n-propanol, and iso-propanol.

The first organosilicon functionalizing agent comprises a halosilane, an organosilane having at least one silanol group and/or an alkoxy group, an aryloxy group, or a cycloalkoxy group; an organosilazane, a cyclic organosiloxane, a low-viscosity polyorganosiloxane that has a silanol group and/or an alkoxy group, an aryloxy group, or a cycloalkoxy group, or a silicone resin that has a silanol group and/or an alkoxy group, an aryloxy group, or a cycloalkoxy group. Examples of alkoxy groups include those groups having 1 to 6 carbon atoms, examples of aryloxy groups include groups having 6 to 10 carbon atoms, and examples of cycloalkoxy groups include groups having 6 to 10 carbon atoms. In an embodiment, the first organosilicon functionalizing agent is selected from the group consisting of a silanol—stopped polydimethylsiloxane, octaphenylcyclotetrasiloxane, octamethylcyclotetrasiloxane ($D_4$) and hexamethyldisilazane (HMDZ). Other examples of the first organosilicon functionalizing agent include diphenylsilanediol, dimethylsilanediol, methyltriethoxysilane, and phenyltrimethoxysilane. The low-viscosity polyorganosiloxane may contain one or more kinds of organic groups selected from the group consisting of a methyl group, a phenyl group, a vinyl group, and a 3,3,3-trifluoropropyl group. Suitable low-viscosity polyorganosiloxanes have a viscosity, as measured at 25° C., in a range of from about 1 to about 300 centipoises in an embodiment, and from about 5 to about 100 centipoises in another embodiment. Examples of the halosilanes include halotrialkylsilanes, such as chlorotrimethylsilane; halotriarylsilanes, such as chlorotriphenylsilane; dichlorodimethylsilane, bis(chlorodimethylsilyl)methane, trichloromethylsilane, bromotrimethylsilane, and the like.

The first reaction mixture is then reacted with a tetraalkoxysilane at a controlled rate to form a second reaction mixture comprising a sol gel silica. The reaction can be carried out by adding the tetraalkoxysilane to the first reaction mixture at a rate so as to maintain the reaction temperature in a range from about 40° C. to about the reflux temperature. In an embodiment, the reaction temperature is maintained in a range from about 40° C. to 100° C. In another embodiment, the reaction temperature is maintained from about 50° C. to about 70° C. The addition of the tetraalkoxysilane is also controlled such that at any given time during this step, the instantaneous mole ratio of the tetraalkoxysilane to the first portion of the first organosilicon functionalizing agent is in a relative mole ratio of from 1:0.2 to about 1:0.6, respectively. Further, without being bound by any theory, it is believed that a controlled rate of addition of the tetraalkoxysilane enables a controlled growth in the size and surface area of the sol gel silica thus produced.

Next, the second reaction mixture comprising the sol gel silica is further reacted with a mixture comprising a second portion of the first organosilicon functionalizing agent and a second organosilicon functionalizing agent. In this step, the sol gel silica is functionalized, wherein the first and the second organosilicon functionalizing agent react with the surface hydroxyl groups on the sol gel silica.

The second organosilicon functionalizing agent comprises at least one organosilicon compound comprising at least one alkenyl group, defined and exemplified as previously described. In another embodiment, the second organosilicon functionalizing agent comprises at least one organosilicon compound comprising one silicon atom having two alkenyl groups bonded to it. In still another embodiment, compounds having two silicon atoms, each of which has one alkenyl group bonded to it can also function as the second organosilicon functionalizing agent. Suitable classes of organosilicon compounds comprising at least one alkenyl group include halodivinylsilanes, dialkyldivinylsilanes, diaryldivinylsilanes, dicycloalkyldivinylsilanes, alkylaryldivinylsilanes, alkoxysilanes, such as for example, (trialkoxy)vinylsilanes; (dialkenyl)silazanes, such as the dialkenyl(tetraalkyl)disilazanes, exemplified by divinyl(tetramethyl)disilazane, (tetraphenyl)(divinyl)disilazane, and the like; cyclic organoalkenylsiloxanes, such as tetramethyltetravinylcyclotetrasiloxane; low-viscosity vinyl-capped polyorganosiloxanes, such as for example, a divinyl-terminated polydimethylsiloxane-polydiphenylsiloxane copolymer having an 84:16 mole ratio of dimethylsiloxane and diphenylsiloxane and a viscosity of about 500 centistokes (available from Aldrich Chemical Company); or a vinyl-capped silicone resin, such as for example, vinyl-capped polydimethylsiloxane having a viscosity from about 850-1150 centistokes (available from Aldrich Chemical Company). Additional examples of cyclic siloxanes can be found in commonly assigned U.S. Pat. No. 6,610,108, published on Aug. 26, 2003, which is herein incorporated in its entirety. Further, each of these classes of compounds may additionally comprise a silanol group and/or an alkoxy group, an aryloxy group, or a cycloalkoxy group. In a particular embodiment, the second organosilicon functionalizing agent comprises divinyl(tetramethyl)disilazane.

The process for producing the functionalized silica further comprises adjusting the relative mole ratio of the first and the second portions of the first organosilicon functionalizing agent. Without being bound by theory, it is believed that the amount of the first portion of the organosilicon functionalizing agent governs the particle size (abbreviated as PS) of the sol gel silica formed in the second step reaction with the tetraalkoxysilane (discussed previously), and the amount of the second portion of the first organosilicon functionalizing agent governs the viscosity of the curable silicone resin, whose preparation is discussed further below in the present disclosure. In an embodiment, the relative mole ratio of the first portion and the second portion of the first organosilicon functionalizing agent can be from about 1:0.5 to about 1:1, respectively. When greater than about 1 mole of the second portion, relative to one mole of the first portion is used, the final cured silicone resin composition generally has less desirable mechanical properties, such as modulus. When less than about 0.5 mole of the second portion, relative to one mole of the first portion is used, gel formation occurs in the final cured silicone resin composition, thereby affecting properties such as transparency and mechanical properties.

Furthermore, the process for producing the functionalized silica further comprises adjusting a relative mole ratio of the first portion of the first organosilicon functionalizing agent and the tetraalkoxysilane. In an embodiment, the relative mole ratio is from about 1:0.2 to about 1:0.6, respectively. When the amount of the first portion of the first organosilicon functionalizing agent is less than 0.2 mole, relative one mole of the tetraalkoxysilane, the resulting functionalized silica particles have an undesirably large particle size that can be generally greater than 30 nanometers, sometimes greater than 50 nanometers. When the amount of the first portion of the first organosilicon functionalizing agent is greater than 0.6 mole, relative to one mole of the tetraalkoxysilane, the resulting functionalized silica generally comprises a collapsed silica network with very little or no formation of discrete particles. The morphology of the silica particles can be studied using TEM (transmission electron microscopy).

The functionalization of the sol gel silica occurs by reaction of the surface hydroxyl groups present in the sol gel silica (formed as described previously) with the second portion of the first organosilicon functionalization agent and the second organosilicon functionalizing agent. The process is also referred to as a hydrophobizing step, whereby the polar silanol hydroxyl groups are converted into hydrophobic groups, such as trialkylsiloxy groups. Such reactions can assist in preventing a subsequent condensation reaction among the sol gel silica particles. Further, during the preparation of low viscosity curable silicone rubber compositions, as discussed further below in the present disclosure, such reactions also assist in preventing reaction between the functionalized silica particles and the silicone polymer, thereby reducing the time required for ageing of the silicone polymer, to prevent creep hardening, and/or to regulate plasticity.

The type of catalyst to be used in preparing the functionalized silica depends upon the type of the first and the second organosilicon functionalizing agents used. For example, when a halotrialkylsilane is used as the first organosilicon functionalizing agent, and a (dialkenyl)halosilane or a (monoalkenyl)halosilane is used as the second organosilicon functionalizing agent, an acid catalyst or a neutral catalyst can be used, since the halosilane upon hydrolysis produces acidic hydrogen halide. Examples of the acid catalyst include aqueous mineral acids, such as hydrochloric acid. Neutral catalysts include water or water-alcohol mixtures can also be used. But, when the first and the second organosilicon functionalizing agents are a silazane compound, such as for example, hexamethyldisilazane and (divinyl)(tetramethyl)silazane (abbreviated as DVTMDZ), respectively, a base catalyst or a neutral catalyst is used. Base catalysts known in the art can be used. An exemplary base catalyst is aqueous ammonia.

After forming the functionalized silica particles in the aqueous alcoholic medium, the resulting product mixture is generally aged by being allowed to stand for a period of time at ambient temperature. The aging period can range from a minimum of about 1 hour to about 15 hours. Generally, the aging period ranges from about 4 hours to about 6 hours.

Next, the aged product mixture is treated with a solvent and heated to remove the water. Solvents that can be used include, for example, hydrocarbons, silicone based monomers, liquid carbon dioxide, and ionic liquids. Some examples of ionic liquids are the imidazolium salts and the pyridinium salts, such as for example, 1-hexyl-3-alkylimidazolium chloride, 1-hexyl-3-alkylimidazolium iodide, 1-hexyl-3-alkylimidazolium hexafluorophosphate, 1-hexyl-3-alkylimidazolium hexafluorophosphate, 1-butyl-3-methylimidazolium octyl sulfate, 1-butyl-3-methylimidazolium 2-(2-methoxyethoxy) ethyl sulfate, 1-ethyl-3-methylimidazolium tosylate, 1-methyl-3-octylimidazolium chloride, and 1-butyl-4-methylpyridinium tetrafluoroborate.

Suitable solvents include those that can form an azeotrope with water, and those that do not. When a solvent that does not form an azeotrope with water is used, it is usually a higher boiling solvent such that water can be removed by fractional distillation. Any hydrocarbon solvent can be used. When a hydrocarbon solvent is used, it can be chosen so as to remove water as an azeotrope. In an embodiment, hydrocarbon solvents having a boiling point higher than that of water and the alcohol comprising the aqueous alcoholic reaction medium can be used. In another embodiment, hydrocarbon solvents having a lower boiling point, but which can form azeotropes with the water and the alcohol can be used. Xylene is an exemplary solvent since it has a higher boiling point than that of water and an aliphatic alcohol, such as ethanol; and it forms an azeotrope with water, thereby facilitating removal of all the water. Other non-limiting examples of suitable hydrocarbon solvents include toluene, cyclohexane, heptane, octane, and iso-octane and isododecanol.

In another embodiment, silicone based monomers having higher boiling point, which can form or do not form azeotropes with the water and the alcohol can be used. Examples of these silicone based monomers include, for example, the cyclic siloxanes such as, hexamethylcyclotrisiloxane (commonly referred to as "$D_3$"), octamethylcyclotetrasiloxane (commonly referred to as "$D_4$"), and decamethylcyclopentasiloxane ("$D_5$"), respectively, and siloxanes, such as, MD, wherein D is $(CH_3)_2Si-O_{2/2}$, and M is $(CH_3)_3Si-O_{1/2}$ are some of the exemplary solvent for silicone based monomers.

After the removal of water, a suspension of the functionalized silica in the solvent is obtained which may contain trace levels of water and/or the alcohol. The suspension of the functionalized silica in the solvent has a high transparency of greater than about 90 percent over a wavelength range of 350 nanometers to 800 nanometers, as measured by UV-visible spectroscopy on a 0.1 weight percent suspension of the functionalized silica in xylene solvent. Further, the functionalized silica has a particle size in a range from about 4 nanometers to about 1000 nanometers with a mean particle size from about 50 nanometers to about 150 nanometers in an embodiment, and a mean particle size from about 80 nanometers to about 120 nanometers in another embodiment. On a dry basis, the functionalized silica can have a concentration of between about 8 to about 2 available silanol hydroxyl groups per square nanometer of the silica in an embodiment, and between about 7 to about 3 silanol hydroxyl groups per square nanometer of filler in another embodiment. The functionalized silica has a BET surface area of 100 meters square per gram to about 1000 meters square per gram in an embodiment, from 200 to 800 meters square per gram in another embodiment, and from 250 to 600 meters square per gram in still another embodiment.

Example A, as displayed in Table 1, provides data which shows that it is preferable to carry out the addition of the first organosilicon functionalizing agent in a staged manner. In Example A the mole ratio of the first portion of the first organosilicon functionalizing agent (HMDZ(I)) to tetraethoxysilane (TEOS) is kept constant at 0.47. In Example A the second portion of the first organosilicon functionalizing agent is presented as HMDZ(II). PDMS-1 is used to form the curable silicone rubber composition of Example A and Comparative Example B. Example A shows the stepwise addition of HMDZ(I) and HMDZ(II) and resulting functionalized silica after being incorporated in the PDMS and subsequently cured gives a cured silicone rubber composition having increased tensile strength (measured in megapascals) and transparency as compared to the corresponding silicone rubber compositions comprising the silica filler where the HMDZ is added in one portion (i.e., Comparative Example B).

TABLE 1

| | HMDZ (I) (milliliters) | HMDZ(II) (milliliters) | Physical properties of the cured silicone rubber composition | | |
|---|---|---|---|---|---|
| | | | Tensile strength | Percent light transmission | Percent elongation |
| Example A | 15.6 | 8.4 | 4.3 | 91.1 | 296 |
| Comparative Example B | 24 | 0 | 2.3 | 93 | 185 |

The suspension of the functionalized silica in a suitable solvent and a silicone polymer can be compounded and devolatilized to form a curable silicone rubber composition. The functionalized silica serves to reinforce the silicone polymer, and is also sometimes referred to as a hydrophobic reinforcing silica filler. Use of semi-continuous or a continuous process can be employed. In a batch process, silicone polymer, the dispersion of the functionalized silica in a suitable solvent, e.g., hydrocarbon solvent or silicone based monomer solvent, and optionally other additives that further enhance the performance, but do not adversely affect the haze of the cured compositions are kneaded by means of a kneading machine such as a planetary mixer, a Ross mixer, a Banbury mixer, a turbulizer, a change can mixer, or a low intensity double arm dough mixer to form the curable silicone rubber composition having the desired properties are obtained. The hydrocarbon solvent or silicone based monomer solvent, generally facilitate better dispersion and mixing of the functionalized silica with the silicone polymer. The batch mixing process can take 12 to 30 hours per batch. After mixing, the curable silicone rubber composition is stripped of volatiles, primarily the hydrocarbons or silicone based monomers and traces of water and/or alcohol, and then cooled to furnish the curable silicone rubber composition. Additional treatment of the curable silicone rubber composition can be carried out to further lower the viscosity of the curable silicone rubber composition, and improve the tensile strength of the cured silicone rubber composition obtained therefrom. In an embodiment, the additional treatment comprises treating the curable silicone rubber composition with a mixture of the first organosilicon functionalizing agent (example: HMDZ) and water at ambient temperature, and heating the resulting mixture under vacuum. In an embodiment, the mixture can be heated to a temperature of about 100° C. Heating at even higher temperatures, up to about 150° C. under vacuum is beneficial in providing curable silicone resin compositions having even lower viscosity, and cured compositions having an even higher tensile strength.

Batch production of cured silicone rubbers can also be done using a two-roll mill. The sheets thus formed can be further heated in air-ventilated ovens.

Continuous processes can also be used for producing curable silicone rubber compositions. In one embodiment, a suspension of the functionalized silica filler in solvents, such as, hydrocarbon solvent or silicone based monomer solvent, the silicone polymer, and optional additives are introduced into an extruder, where they are continuously compounded and devolatilized into a curable liquid silicone rubber composition. Examples of silicone polymers include the polydimethylsiloxanes PDMS-1 having a viscosity of 10 pascal second, and PDMS-2 having a viscosity of 65 pascal second, when measured under a shear rate of 10 radians per second.

The silicone polymer used in the compositions of the present invention is typically a vinyl-terminated polydimethylsiloxane having a viscosity varying from 0.1 to 2000 pascal-second at 25° C. in an embodiment, and from 0.1 to 200 pascal-second at 25° C. in another embodiment. The silicone polymer can be represented by recurring units of Formula I:

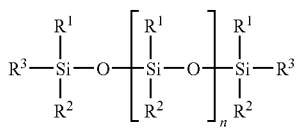

Formula I wherein $R^1$ independently at each occurrence represents an alkyl containing from 1 to 4 carbon atoms, or an alkylene containing 2 to 4 carbon atoms; $R^2$ independently at each occurrence represents an alkyl containing from 1 to 4 carbon atoms, a haloalkyl containing from 1 to 4 carbon atoms, or an alkylene containing from 2 to 4 carbon toms; $R^3$ independently at each occurrence represents a H, an alkyl containing from 1 to 10 carbon atoms, an alkylene containing from 2 to 4 carbon atoms, a cycloalkyl containing from 4 to 6 carbon atoms, an OH, or a haloalkyl containing from 1 to 4 carbon atoms; and n represents an integer so that the viscosity of the silicone polymer varies from 0.1 to 2000 pascal-second at 25° C. Broadly, n can be about 80 to about 3500, desirably, n is a value of about 100 to less than 1000. In an embodiment, the silicone polymer has a formula I, wherein $R^1$ independently at each occurrence represents a $CH_3$ or a $CH=CH_2$; $R^2$ independently at each occurrence represents a $CH_3$, a $CH=CH_2$; a $CH_2$, or a $CH_2CH_2CF_3$; $R^3$ independently at each occurrence represents a $CH_3$, $CH=CH_2$, an OH, or a $CH_2CH_2CF_3$; and n represents an integer from about 200 to about 900. In still another embodiment, the silicone polymer has a vinyl content ranging from about 0.05 percent to about 0.5 percent by weight of the silicone polymer.

In the preparation of the curable silicone rubber composition, the amount of the functionalized silica on a dry basis can be from about 10 to about 50 parts by weight in an embodiment, from about 30 to about 50 parts by weight in another embodiment, and from about 20 to about 50 parts by weight in still another embodiment, per 100 parts by weight of the silicone polymer. If necessary during the compounding and devolatilizing step, the content of the functionalized silica can be adjusted by adding a requisite amount of the silicone polymer, by adding more of the suspension of the functionalized silica in the solvent, or by adding a fumed silica, such as those known in the art or commercially available. For example, Aerosil 300 is an example of a commercially available fumed silica that can be used in the silicone rubber compositions disclosed herein. Thus, in an embodiment, curable silicone rubber compositions having a combination of desirable mechanical properties, transparency, and percent elongation can be produced by using a combination comprising a fumed silica and the functionalized silica.

The functionalized silica and the techniques described hereinabove are especially useful for producing curable liquid silicone rubber (abbreviated as "LSR") compositions having a low shear viscosity from about 200 pascal-second to about 1500 pascal-second in an embodiment, and from about 500 pascal-second to about 1000 pascal-second in another embodiment, when measured at 10 radians per second in accordance with ASTM D440 test method. Further, these low viscosity LSR compositions are pumpable, which facilitates their use in commercial operations, especially in continuous productions processes. In an embodiment, a co-rotating, intermeshing double screw extruder can be used for a continuous operation. Generally, the extruder is operated at a temperature in the range of 160-210° C., and a pressure between about 70 and about 300 pounds per square inch (psi). Stripping of volatiles can be effected toward the end of the extruder while the material is hot thereby eliminating secondary operations. Filtration can be done at the discharge of the extruder while the material is hot, eliminating secondary operations. Cooling and de-airing can be implemented in a separate counter-rotating mixer, which can provide back-mixing and a high residence time to effectively homogenize the material into a base material. Some techniques for continuously producing a LSR composition are disclosed in commonly assigned U.S. Pat. Nos. 6,749,786, and 6,444,154, which are herein incorporated in their entirety.

In another aspect, the present disclosure provides a method for producing a cured silicone rubber composition. The method comprises further compounding and devolatilizing the curable silicone rubber composition, described previously, to form the cured silicone rubber composition. The equipment that was previously described for producing the curable silicone rubber compositions in a batch or a continuous process can also be used for producing the cured silicone rubber compositions. Continuous processes can be implemented using a co-rotating, intermeshing double screw extruder and the procedures disclosed in commonly assigned U.S. Pat. Nos. 6,749,786, and 6,444,154, which are herein incorporated in their entirety.

In an embodiment, the base curable silicone rubber composition, prepared as previously described, can be divided into two components and separately mixed in static mixers with catalyst and other additives to produce two component mixtures, "A" and "B". The two components can be made simultaneously to reduce inventories. In an embodiment, component A may comprise from 95-97 weight percent of the curable LSR composition, relative to an overall weight of component A, a curing catalyst, and other suitable additives that further enhance the performance, but do not adversely affect the haze of the cured compositions. Examples of additives that may be added include adhesion promotion adhesives, heat stabilizers, UV stabilizers, plasticizers, and colorants that color, but do not increase haze value. Component B may comprise from 95-97 weight percent of the curable LSR composition, relative to an overall weight of component B and a cross-linker. Then the components A and B are injected into a mold to produce a cured silicone rubber part. Compression molding techniques can be used, wherein the blended curable silicone rubber composition is injected into a molding chase or other molding devices known in the art, and molded into plaques or discs. In another embodiment, the curable silicone rubber composition and the latent form of the catalyst are first blended for a suitable period of time, then a cross-linker, such as an organohydrogensiloxane is added and further blended, usually under vacuum, until no more air bubbles are present in the mixture. One of skill in the art will appreciate that the techniques of compression molding can be optimized using process parameters, such as pre-heating time, compression time, compression pressure, compression temperature, and cooling time.

The curing step can be implemented by heating alone, heating under pressure, by using a curing catalyst, by moisture, or by exposing the composition to a radiation. Any curing catalyst commonly known in the art for forming covalent bonds between the silicone polymer and the functionalized silica can be used. Generally, the catalyst aids in forming covalent bonds between the surface alkenyl groups of the functionalized silica and the alkenyl groups of the silicone polymer. The curing catalyst can be a free radical initiator, such as an organic peroxide or an organic azo compound. Examples of peroxide catalysts include benzoyl peroxide, 2,5-dimethyl-2,5-di(tert-butylperoxy)hexane, and the like. The catalyst can also be an organometallic complex of a transition metal, such as platinum, which is generally used as a hydrosilylation catalyst. Usually, the platinum catalyst is introduced in a latent form such that the active form can be generated by application of an external stimulus, such as thermal energy or photochemical energy. For example, a platinum complex of 1-ethynyl-cyclohexan-1-ol can be used as the latent form of the catalyst in the curing step. When the curable silicone rubber composition is heated in the curing step, the platinum complex releases 1-ethynyl-cyclohexan-1-ol, thereby releasing an active form of the platinum catalyst. Other catalysts known in the art can also be used. Mixtures of catalysts can also be used.

The cured silicone rubber compositions generally comprise from about 5 to about 60 weight percent in an embodiment, and from about 10 to about 30 weight percent in another embodiment, of the functionalized silica chemically bonded to the silicone polymer matrix. Further, in an embodiment, the cured compositions and cured parts have a high transparency of greater than 90 percent light transmission, as measured on a 2.3 millimeters thick plaque using ASTM D1003 test method. In another embodiment, the cured compositions and cured parts have a tensile strength of greater than 5 megapascals as measured using ASTM D612 test method. In yet another embodiment, the cured compositions and cured parts have an elongation of at least 200 percent as measured using ASTM D612 test method. In still yet another embodiment, cured products having a desirable combination of all three listed physical properties can be produced.

A variety of end-use products can be produced from the curable silicone resin compositions. Product include, for example, compression molded sheet, diving mask, infant nipple, a face mask, a surgical tubing, a pacifier, a light emitting diode, or a disposable ocular lens.

While only certain features of the invention have been illustrated and described herein, many modifications and changes will occur to those skilled in the art. It is, therefore, to be understood that the appended claims are intended to cover all such modifications and changes as fall within the true spirit of the invention.

EXAMPLES

The BET surface area meter of the silica powder was measured on a degassed sample using Micromeretics ASAP 2010 by nitrogen adsorption. Percent light transmittance on the cured silicone rubber sheets was measured with a BYK—Gardner "Haze gard" instrument by using 2.3 millimeter thick sheets.

Unless otherwise indicated, the viscosity values shown in the following Tables are for the curable silicone rubber compositions, and are given in pascal-second when measured at 10 radians per second in accordance with ASTM D440 test method. Tensile strength, given in megapascals; percent light transmittance, and percent elongation are given for the cured silicone rubber compositions. Viscosity errors are +/−10 percent.

Example 1

Procedure for Preparing a Functionalized Silica of the Invention

The functionalized silica of Example 1 was prepared as follows: Into a three-necked round-bottomed flask equipped with a mechanical stirrer and heated with an oil bath maintained at 67° C. was taken ethanol (250 milliliters), 25 weight percent aqueous ammonia solution (53 milliliters), water (15 milliliters), followed by HMDZ (15.6 milliliters). After the addition of HMDZ, the contents of the reaction flask was mixed for 8 minutes. Then TEOS was added at the rate of 7 milliliters per minute by using a peristaltic pump. After 120 milliliters of TEOS had been added, the resulting reaction mixture was stirred for 30 minutes. Then a mixture of HMDZ (15 milliliters) and 1,3-divinyl-1,1,3,3-tetramethylsilazane (DVTMDZ) was added to the reaction mixture at the rate of 4 milliliters per minute. After the addition, the resulting mixture was heated under reflux for about 1.5 hours. Then the heating was stopped, and the resulting mixture was stirred overnight while being allowed to cool to ambient temperature. This step is sometimes referred to as an "aging" step. Next, the mixture was treated with 200 milliliters of xylene (or octamethylcyclotetrasiloxane ($D_4$)), and the mixture was heated until about 250 to 300 milliliters of a distillate had been collected. During the distillation, almost all of the ethanol and ammonia was removed and the pH of the contents in the distillation flask was about 7. The material in the reaction flask contained a suspension of the desired functionalized silica in xylene (or $D_4$). The color of the suspension varied from a milky colloid to a water clear transparent liquid.

The above Example was carried out using various rates of addition of TEOS. Suspensions comprises up to about 20 weight percent of the functionalized silica were prepared.

The functionalized silica of Comparative Example 1 was prepared with the same quantities of the various reactants as in Example 1, however, the HMDZ addition was not performed in a stepwise fashion.

Into a three-necked round-bottomed flask equipped with a mechanical stirrer were added ethanol (250 milliliters), 25 weight percent aqueous ammonia solution (53 milliliters), water (15 milliliters), HMDZ (30.6 milliliters), DVTMDZ (0.3 milliliter), and finally TEOS (120 milliliters) in the indicated sequence at ambient temperature. After being stirred overnight at ambient temperature, the suspension of the functionalized silica in xylene (or $D_4$) was obtained as described in Example 1.

The particle size of the functionalized silica was measured using the following procedure. A portion of the suspension in xylene was diluted with ethanol to obtain a 1 weight percent suspension. After being irradiated in an ultrasound bath for 5 minutes, the suspension was taken in a quartz cuvette of a Horiba LB 500 instrument and the particle size (PS) and particle size distribution (PSD) were measured.

The functionalized silica of Example 1 showed a mean PS of about 90 nanometers and a PSD with a maximum and a minimum particle size between about 40 nanometers and less than 1000 nanometers. The functionalized silica of Comparative Example 1 showed that the particles had a minimum size of greater than 5000 nanometers.

Curable silicone resin composition using the functionalized silica of Example 1 and Comparative Example 1 were prepared combining the functionalized silica with a vinyl-terminated polydimethylsiloxane (abbreviated as "PDMS"), such as a PDMS having a viscosity of 10 pascal second at a shear rate of 10 radians per second, herein named as PDMS-1, or a PDMS having a viscosity of 65 pascal second at a shear rate of 10 radians per second, herein named as PDMS-2. Vinyl-terminated polydimethylsiloxane was combined with the functionalized silica of Example 1 and Comparative Example 1 in a planetary mixer or a Ross mixer so as to obtain a dosage of the functionalized silica of about 10 to about 40 weight percent. After being mixed at a temperature of 70-150° C. for 120 minutes, a curable silicone rubber composition was obtained as a viscous liquid material.

of the first organosilicon functionalizing agent, represented as HMDZ(II)/HMDZ(I); and the relative mole ratio of the first portion of the first organosilicon functionalizing agent to the tetraalkoxysilane, represented as HMDZ(I)/TEOS. Examples 4-6 were prepared as described in Example 1. The results of the various HMDZ(II)/HMDZ(I) and HMDZ(I)/TEOS ratios of Examples 4-6 are presented in Table 3. The weight percent of the functionalized silica in the curable silicone composition in Examples 4-6 was 25 weight percent. The TEOS feed rate was 7.5 ml/min in Example 4, 7 ml/min in Example 5, and 6 ml/min in Example 6.

TABLE 3

|  | HMDZ(II)/ HMDZ(I) mole ratio | HMDZ(I)/ TEOS mole ratio | Viscosity | Physical properties of the cured silicone rubber composition | | |
|---|---|---|---|---|---|---|
|  |  |  |  | Tensile strength | Percent light transmission | Percent elongation |
| Example 4 | 0.96 | 0.29 | 1128 | 6.5 (0.4) | 92.3 | 437 (34) |
| Example 5 | 0.77 | 0.29 | 1352 | 6.8 (0.3) | 92.8 | 440 (16) |
| Example 6 | 0.54 | 0.29 | 1619 | 4.3 (0.7) | 91.1 | 296 |

Cured silicone rubber composition were prepared using the curable silicone resin composition of Example 1 and Comparative Example 1 as follows: the curable liquid silicone rubber materials, prepared as described above were combined with a cross-linker, and an inhibited platinum catalyst, and cured at 175° C. for 10 minutes in a 30 cm*30 cm*2.3 mm stainless steel plate using a compression molding machine. The sheets may be optionally post-cured in a air-circulated oven maintained at 200° C. for 4 to 8 hours.

The viscosities of the curable silicone rubber compositions of Example 1 and Comparative Example 1 and physical properties of the cured silicone rubber compositions, respectively, are displayed in Table 2. The weight percent of the functionalized silica in the curable silicone compositions of Example 1 and Comparative Example 1 was 25 weight percent.

As the HMDZ(II)/HMDZ(I) mole ratio increases and approaches 1, the viscosity of the curable silicone resin decreases, thus changing significantly the rheology aspects related to processibility. (see Table 3)

Comparative Examples 2, 3, and Example 7 were prepared to illustrate curable silicone rubber compositions treated to produce curable silicone rubber compositions having significantly reduced viscosity without compromising the properties of the cured composition, such as tensile strength, transparency, and percent elongation.

Comparative Example 2 was prepared by the procedure of Example 1 except that the TEOS addition rate was maintained at 4 milliliters per minute to produce a xylene dispersion of a functionalized silica. This material was mixed with PDMS-2 in a Ross mixer using the procedure described above to fur-

TABLE 2

|  | PDMS used | Viscosity of curable silicone rubber composition | Physical properties of the cured silicone rubber composition | | |
|---|---|---|---|---|---|
|  |  |  | Tensile strength (megapascals) | Percent light transmission | Percent elongation |
| Example 1 | PDMS-2 | 750 | 5.9 (0.1) | 92.8 | 393 (8) |
| Comparative Example 1 | PDMS-2 | 130 | 1.1 (0.2) | 85.5 | 199 (19) |

As represented by the data presented in Table 2 the cured silicone rubber composition of Example 1 displayed a higher tensile strength, higher transparency, and a higher viscosity (i.e., in the range of 500-1500 pascal-second), compared to the corresponding silicone rubber compositions comprising the functionalized silica of Comparative Example 1.

Examples 4-6 were prepared to demonstrate the effect of the relative mole ratio of the second portion to the first portion nish the curable silicone resin composition of Comparative Example 2 which contained 25 weight percent of the functionalized silica. The curable silicone resin composition of Comparative Example 2 was cured to provide the corresponding cured compositions.

Comparative Example 3 was prepared with the curable resin composition of Comparative Example 2, which was cooled to room temperature and treated with HMDZ (7 weight percent relative to the total amount of HMDZ used in Comparative Example 2), followed by water (3.5 weight percent relative to the total amount of HMDZ used in Comparative Example 2). The resulting mixture was stirred under vacuum, first at a temperature of 40° C. for 30 minutes, and then at a temperature of 100° C. for 30 minutes to provide the curable silicone resin composition of Comparative Example 3, which contained 25 weight percent of the functionalized silica. The curable silicone resin composition of Comparative Example 3 was cured to provide the corresponding cured compositions.

Example 7 was prepared with the curable resin composition of Comparative Example 3, obtained as described above, which was further heated to a maximum temperature of 150° C. for 30 minutes under vacuum, and then cooled to ambient temperature to provide the curable silicone resin of Example 7 which contained 25 weight percent of the functionalized silica. The curable silicone resin composition of Example 7 was cured to provide the corresponding cured compositions.

The properties of the curable compositions and the corresponding cured compositions of Comparative Examples 2-3 and Example 7 are displayed in Table 4.

TABLE 4

| | Physical properties of the cured silicone rubber compositions | | | |
|---|---|---|---|---|
| | Viscosity | Tensile strength | Percent light transmission | Percent elongation |
| Comparative Example 2 | 2588 | 6.8 (0.1) | 92.8 | 490 |
| Comparative Example 3 | 1644 | 7 (0.4) | 92.8 | 507 |
| Example 7 | 1378 | 7.2 (0.4) | 92.8 | 502 |

The data as presented in Table 4 show that the viscosity of the curable silicone resin composition produced initially can be further lowered to a value within the desired range of 500-1500 pascal-second, but without affecting the tensile strength and percent elongation by carrying out a treatment with HMDZ and water, followed by heating to a temperature from about 100° C. to about 150° C.

Comparative Examples 4 and Examples 8 illustrate the beneficial effects of adding a curable silicone rubber composition comprising a fumed silica filler known in the art on the properties of the curable and cured silicone rubber compositions disclosed herein. The results are displayed in Table 5.

Comparative Example 4 was prepared with a curable silicone rubber composition comprising LSR 2030 and the cured composition therefrom. LSR 2030 is a commercially available material, which has 24 weight percent of Aerosil 300 fumed silica dispersed in PDMS-2.

Example 8 was prepared with a curable silicone rubber composition comprising equal weights of a 24 weight percent of the functionalized silica of Example 5 dispersed in PDMS-2; and LSR 2030 curable silicone resin composition; and a cured composition obtained therefrom.

TABLE 5

| | Weight percent of silica filler in curable composition | Properties of cured silicone rubber composition | | | |
|---|---|---|---|---|---|
| | | Viscosity | Percent light transmission | Tensile strength | Percent elongation |
| Comparative Example 4 | 24 | 540 | 89-90 | 7.0 | 900 |
| Example 8 | 24 | 620 | 91.5 | 7.6 (0.7) | 580 (32) |
| Example 5 | | 1352 | 92.8 | 6.8 (0.3) | 440 (16) |

The results of Example 5 (from Table 3 herein above) are presented in Table 5 with the results obtained for Comparative Example 4 and Example 8, which shows that the cured silicone composition of Example 5 gives a higher percent light transmission of greater than 90 percent as compared with the composition of Comparative Example 4. Further, Example 8 comprising a combination of LSR 2030 curable silicone rubber composition and the dispersion of the functionalized silica of Example 5 in PDMS-2 gives a superior percent light transmission as compared to the composition of Comparative Example 4. Furthermore, the results obtained with Examples 5 and 8 illustrate that by using a fumed silica-reinforced silicone rubber such as LSR 2030, one can lower the viscosity of the curable silicone rubber composition from 1352 to 620 pascal-second without adversely affecting the percent light transmission and tensile strength.

Comparative Example 6 was prepared with commercially available MQ resin available from GE Silicones of GE Advanced Materials. The MQ is a three-dimensional particulate silicone resin having an average size from less than 1 nanometer to 2 nanometers. The MQ was dispersed in PDMS-1 to provide a 25 weight percent dispersion of a curable silicone resin composition. The cured composition was then prepared. The properties measured were as follows: Viscosity of the curable composition=100-200 pascal-second; tensile strength of the cured composition=0.5-1 megapascal; percent light transmission=greater than 93 percent; percent elongation=100-150 percent.

While the invention has been described with reference to a preferred embodiment, those skilled in the art will understand that various changes may be made and equivalents may be substituted for elements thereof without departing from the scope of the invention. It is intended that the invention not be limited to the particular embodiment disclosed as the best mode for carrying out this invention, but that the invention will include all embodiments falling within the scope of the appended claims. All citations referred herein are expressly incorporated herein by reference.

The invention claimed is:

1. A method for preparing a functionalized silica, comprising:
   mixing an aqueous alcoholic solution and a catalyst with a first portion of a first organosilicon functionalizing agent to form a first reaction mixture;
   reacting said first reaction mixture with a tetraalkoxysilane at a controlled rate to form a second reaction mixture comprising a sol gel silica; and
   further reacting said second reaction mixture with a mixture of a second portion of said first organosilicon functionalizing agent and a second organosilicon functionalizing agent to functionalize the sol gel silica to form said functionalized silica.

2. The method of claim 1 further comprising adding at least one additional solvent wherein a suspension is formed comprising said functionalized silica.

3. The method of claim 2 wherein the solvent is selected from the group consisting of hydrocarbons, silicone based monomers, liquid carbon dioxide, ionic liquids and mixtures thereof.

4. The method of claim 3 wherein said hydrocarbon solvent is selected from the group consisting of xylene, toluene, cyclohexane, heptane, octane, iso-octane, isododecanol and mixtures thereof.

5. The method of claim 3 wherein the silicone based monomer solvent is selected from the group consisting of hexamethylcyclotrisiloxane, octamethylcyclotetrasiloxane, decamethylcyclopentasiloxane and mixtures thereof.

6. The method of claim 1 wherein the first organosilicon functionalizing agent comprises a organosilazane, and the catalyst comprises a base catalyst or a neutral catalyst.

7. The method of claim 6 wherein the organosilazane comprises a hexaalkyldisilazane.

8. The method of claim 7 wherein said catalyst comprises a base catalyst.

9. The method of claim 7 wherein said hexaalkyldisilazane comprises hexamethyldisilazane.

10. The method of claim 1, wherein said first organosilicon functionalizing agent comprises a halosilane, and said catalyst is an acid catalyst or a neutral catalyst.

11. The method of claim 10, wherein said dialkenyl(tetraalkyl)disilazane comprises divinyl(tetramethyl)disilazane.

12. The method of claim 1, wherein said second organosilicon functionalizing agent comprises at least one alkenyl group.

13. The method of claim 12, wherein said second organosilicon functionalizing agent comprises a (dialkenyl)disilazane.

14. The method of claim 13, wherein said (dialkenyl)silazane comprises a dialkenyl(tetraalkyl)disilazane.

15. The method of claim 1, wherein said second organosilicon functionalizing agent comprises a (alkenyl)halosilane, and said catalyst is an acid catalyst or a neutral catalyst.

16. The method of claim 1, wherein said second portion and said first portion of said first organosilicon functionalizing agent are employed in a relative mole ratio of from about 1:0.5 to about 1:1.

17. The method of claim 1, wherein said tetraalkoxysilane and said first portion of said first organosilicon functionalizing agent are in a relative mole ratio of from 1:0.2 to about 1:0.6.

18. A method for forming a curable silicone rubber composition, comprising:
a) forming a functionalized silica by a method comprising:
mixing an aqueous basic alcoholic solution with a first organosilicon functionalizing agent to form a first reaction mixture;
reacting said first reaction mixture with a tetraalkoxysilane at a controlled rate to form a second reaction mixture comprising a sol gel silica;
further reacting said second reaction mixture with a mixture of a second portion of said first organosilicon functionalizing agent and a second organosilicon functionalizing agent to form the functionalized silica;
b) adding a solvent to the mixture of (a) wherein a suspension is formed comprising the functionalized silica; and
c) compounding and devolatilizing said suspension of (b) with a silicone polymer to form said curable silicone rubber composition.

19. The method of claim 18, wherein said curable silicone rubber composition is a curable liquid silicone rubber composition.

20. The method of claim 18, further comprising treating said curable silicone rubber composition with a further portion of said first organosilicon functionalizing agent.

21. The method of claim 20, further comprising heating to a temperature from greater than 100° C. to about 150° C. under vacuum.

22. A curable silicone rubber composition prepared in accordance with the method of claim 18.

23. The curable silicone rubber composition of claim 22, having a shear viscosity from about 200 pascal-second to about 1500 pascal-second, when measured at 10 radians per second in accordance with ASTM D440 test method.

24. The curable silicone rubber composition of claim 22, having a shear viscosity from about 500 pascal-second to about 1000 pascal-second, when measured at 10 radians per second in accordance with ASTM D440 test method.

25. The curable silicone rubber composition of claim 18, further comprising a fumed silica.

26. A method for forming a cured silicone rubber composition, comprising:
forming a functionalized silica by a method comprising:
mixing an aqueous basic alcoholic solution with a first organosilicon functionalizing agent to form a first reaction mixture;
reacting said first reaction mixture with a tetraalkoxysilane at a controlled rate to form a second reaction mixture comprising a sol gel silica;
further reacting said second reaction mixture with a mixture of a second portion of said first organosilicon functionalizing agent and a second organosilicon functionalizing agent to form the functionalized silica;
adding a solvent wherein a suspension is formed comprising the functionalized silica;
compounding and devolatilizing said suspension with a liquid silicone polymer to form a curable silicone rubber composition; and
further compounding and devolatilizing said curable silicone rubber composition to form said cured silicone rubber composition.

27. The method of claim 26, further comprising dividing said curable silicone rubber composition into a first stream and a second stream.

28. The process of claim 27, wherein a platinum catalyst is added to said first stream to produce a component mixture A and a cross-linker is added to said second stream to produce a component mixture B.

29. The process of claim 28, comprising injecting and curing said component mixture A and said component mixture B into a mold to produce a cured silicone rubber part.

30. The method of claim 26, wherein compounding and devolatilizing said curable silicone rubber composition is implemented in a co-rotating, intermeshing double screw extruder.

31. A cured silicone rubber composition prepared in accordance with the method of claim 26.

32. The cured silicone rubber composition of claim 31, having a percent light transmission of greater than 90 percent as measured on a 2.3 millimeters thick plaque using ASTM D1003 test method; a tensile strength of greater than 4.5 megapascals as measured using ASTM D612 test method; and an elongation of at least 200 percent as measured using ASTM D612 test method.

33. An article manufactured using the cured silicone rubber composition of claim 32.

34. The article of claim 33, comprising a compression molded sheet, an diving mask, infant nipple, a face mask, a surgical tubing, a pacifier, a light emitting diode, or a disposable ocular lens.

* * * * *